(12) United States Patent
Cao et al.

(10) Patent No.: US 11,304,755 B2
(45) Date of Patent: Apr. 19, 2022

(54) MICROWAVE TISSUE ABLATION PROBE WITH NON-METALLIC INTRODUCER SET

(71) Applicant: Boston Scientific Scimed, Inc., Maple Grove, MN (US)

(72) Inventors: Hong Cao, Maple Grove, MN (US); Kent David Harrison, Maple Grove, MN (US); Timothy A. Ostroot, Cokato, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 206 days.

(21) Appl. No.: 16/385,994

(22) Filed: Apr. 16, 2019

(65) Prior Publication Data

US 2019/0321097 A1 Oct. 24, 2019

Related U.S. Application Data

(60) Provisional application No. 62/659,519, filed on Apr. 18, 2018.

(51) Int. Cl.
*A61B 18/18* (2006.01)
*A61B 18/00* (2006.01)
(Continued)

(52) U.S. Cl.
CPC .......... *A61B 18/1815* (2013.01); *A61B 17/04* (2013.01); *A61B 17/3415* (2013.01);
(Continued)

(58) Field of Classification Search
CPC ... A61M 2025/0681; A61B 2018/1869; A61B 18/1815; A61B 2018/1884;
(Continued)

(56) References Cited

U.S. PATENT DOCUMENTS 4,545,374 A * 10/1985 Jacobson ........... A61B 17/0218
600/210
5,855,576 A   1/1999 Leveen et al.
(Continued)

FOREIGN PATENT DOCUMENTS

JP   2012101080   5/2012
JP   2021519654   8/2021
(Continued)

OTHER PUBLICATIONS

Brace, Christopher L. "Radiofrequency and microwave ablation of the liver, lung, kidney and bone: what are the differences:," "Organ-Specific Thermal Ablation" Curr Probl Diagn Radiol. 2009; 38(3): 135-143 (17 pages).
(Continued)

*Primary Examiner* — Linda C Dvorak
*Assistant Examiner* — Lindsay Regan Lancaster
(74) *Attorney, Agent, or Firm* — Pauly, DeVries Smith & Deffner LLC

(57) ABSTRACT

An introducer set for a microwave ablation probe is disclosed. The introducer set includes a cannula that is at least partially transparent to microwave energy, and a stylet sized to be received by the lumen of the cannula. Other examples provide a microwave ablation system including a microwave ablation probe having a radiating portion and a cannula that is at least partially transparent to microwave energy. The radiating portion of the probe aligns with the transparent portion of the cannula when the probe is inserted into the cannula lumen. The technology provides a method including introducing a microwave ablation probe into the lumen of a cannula having a cannula body that is at least partially transparent to microwave energy, aligning the transparent portion of the cannula with the radiating portion of the probe, and causing microwave energy to be emitted from the radiating portion of the probe.

18 Claims, 8 Drawing Sheets

(51) Int. Cl.
- *A61B 17/34* (2006.01)
- *A61M 25/06* (2006.01)
- *A61B 17/00* (2006.01)
- *A61B 17/30* (2006.01)
- *A61B 17/04* (2006.01)

(52) U.S. Cl.
CPC .............. *A61B 2017/00951* (2013.01); *A61B 2017/306* (2013.01); *A61B 2017/3492* (2013.01); *A61B 2018/00577* (2013.01); *A61B 2018/1823* (2013.01); *A61B 2018/1869* (2013.01); *A61B 2018/1884* (2013.01); *A61M 2025/0681* (2013.01); *A61M 2205/0283* (2013.01)

(58) Field of Classification Search
CPC .. A61B 2018/00023; A61B 2017/3492; A61B 2018/00577; A61B 2017/00951; A61B 2017/306; A61B 17/04; A61B 2017/308; A61B 2017/3407; A61B 90/11; A61B 17/3403; A61B 2018/1892
See application file for complete search history.

(56) References Cited

U.S. PATENT DOCUMENTS

| | | | |
|---|---|---|---|
| 6,306,132 B1 | 10/2001 | Moorman et al. | |
| 6,383,182 B1 | 5/2002 | Berube et al. | |
| 6,575,969 B1 * | 6/2003 | Rittman, III | A61B 18/1482 606/41 |
| 8,059,059 B2 | 11/2011 | Bonn | |
| 9,119,647 B2 * | 9/2015 | Brannan | A61B 18/1815 |
| 9,561,053 B2 * | 2/2017 | Bonde | A61B 17/3468 |
| 9,833,286 B2 | 12/2017 | Podhajsky | |
| 9,867,665 B2 | 1/2018 | Dickhans et al. | |
| 2009/0295674 A1 * | 12/2009 | Bonn | A61B 18/1815 343/872 |
| 2010/0045559 A1 | 2/2010 | Rossetto | |
| 2011/0077633 A1 * | 3/2011 | Bonn | A61B 90/04 606/33 |
| 2012/0123403 A1 * | 5/2012 | Brannan | A61B 18/1815 606/33 |
| 2014/0121658 A1 | 5/2014 | Cosman, Jr. et al. | |
| 2015/0057570 A1 * | 2/2015 | Chin | A61B 10/0283 600/566 |
| 2015/0297246 A1 | 10/2015 | Patel et al. | |
| 2016/0030079 A1 * | 2/2016 | Cohen | A61M 25/0606 604/507 |
| 2016/0135842 A1 | 5/2016 | Kassab | |
| 2016/0278791 A1 * | 9/2016 | Pellegrino | A61B 17/3472 |
| 2017/0245930 A1 * | 8/2017 | Brannan | A61B 18/1815 |

FOREIGN PATENT DOCUMENTS

| | | | |
|---|---|---|---|
| WO | 2006084676 | 8/2006 | |
| WO | WO-2013014583 A1 * | 1/2013 | ............. A61B 18/04 |
| WO | 2019204407 | 10/2019 | |

OTHER PUBLICATIONS

Lubner, Meghan G. et al., "Microwave Tumor Ablation: Mechanism of Action, Clinical Results and Devices," J Vasc Interv Radiol. Aug. 2010; 21(8 suppl): S192-S203 (38 pages).

"International Search Report and Written Opinion," for PCT Application No. PCT/US2019/027827 dated Jul. 17, 2019 (12 pages).

"Response to Communication Pursuant to Rules 161(1) and 162 EPC," for European Patent Application No. 19720349.0 filed Mar. 10, 2021 (9 pages).

"Office Action," for Japanese Patent Application No. 2020-556974 dated Sep. 21, 2021 (15 pages) with English Translation.

"International Preliminary Report on Patentability," for PCT Application No. PCT/US2019/027827 dated Oct. 29, 2020 (8 pages).

* cited by examiner

MICROWAVE TISSUE ABLATION PROBE WITH NON-METALLIC INTRODUCER SET

This application claims the benefit of U.S. Provisional Application No. 62/659,519, filed Apr. 18, 2018, the content of which is herein incorporated by reference in its entirety.

BACKGROUND

Microwave ablation is used in the treatment of certain types medical conditions, including the treatment of tumors. During microwave ablation therapy, an elongated probe is inserted into patient tissue. The probe has a microwave antenna that emits electromagnetic radiation in the microwave frequency spectrum. The electromagnetic radiation heats the tumor cells, causing coagulation and destroying the diseased tissue.

In a microwave ablation system, a generator generates power that is transmitted through the shaft of the probe to the microwave antenna, where the energy is transmitted as radiation to the surrounding tissue. Some microwave ablation probes use a coaxial cable design, with an inner conductor separated from a coaxial outer conductor by a dielectric material. U.S. Pat. No. 8,059,059, entitled "Slidable Choke Microwave Antenna," describes a microwave antenna assembly with a radiating portion including a dipole antenna; this patent is hereby incorporated by reference in its entirety.

One physical restriction that must be overcome in microwave ablation is unwanted heating along the coaxial cable caused by reflected power. Thus, most microwave ablation probes use some type of cooling system to prevent tissue damage along the probe shaft.

The physical properties of microwave ablation probes, such as the diameter, material composition, and flexibility of the probe are constrained by the technical requirements of energy propagation along the probe shaft. For example, although it is desirable to make the diameter of the probe as small as possible to be less invasive to patient tissue, shaft heating due to reflected power increases as the probe diameter decreases. Thus, tradeoffs must be made in the design of microwave ablation systems.

Another design consideration is the ability of the microwave ablation probe to pierce tissue and travel through the tissue to the desired location for ablation. The probe tip must be sufficiently sharp and the probe shaft sufficiently rigid to allow steering the microwave antenna to the correct location.

SUMMARY

Some examples of the disclosed technology include an introducer set for a microwave ablation probe, the microwave ablation probe having an elongated probe body and a radiating portion configured to emit microwave energy. In some examples, the introducer set has a cannula with a cannula body defining a lumen sized to receive the elongated probe body of the microwave ablation probe. In some examples, the cannula body can have a non-metal portion located along the cannula body such that the non-metal portion overlaps the radiating portion of the microwave ablation probe when the microwave ablation probe is inserted into the cannula. In some examples, the introducer set further includes a tissue-penetrating stylet sized to be received by the lumen of the cannula. Alternatively or in addition, the introducer set includes a fixation mechanism configured to fix a location of at least a part of the cannula within or to patient tissue.

Further examples of the disclosed technology can have one or more alternative or additional features. The fixation mechanism can be, for example, a plurality of tines for anchoring the cannula to tissue, a suture, a suction pad, or a self-adhesive pad with a connector. In some examples, the stylet or the cannula of the introducer set has a navigational sensor and/or a navigational marker. In some examples, the stylet of the introducer set has a trocar at a tip of the stylet. In some examples, the cannula is less rigid than the stylet. In some examples, the cannula further has a blunt tip. In some examples, the cannula body is made entirely of a non-metal material. Some examples also include the microwave ablation probe with an elongated probe body that has a blunt tip.

Other examples of the disclosed technology include a microwave ablation system that includes a microwave ablation probe with an elongated probe body and a radiating portion for emission of microwave energy at a distal portion of the probe body. The system includes a cannula having a lumen and a window portion at a distal portion of the cannula, the window portion being at least partially transparent to microwave energy. Alternatively or in addition, some examples provide an introducer set that includes the cannula and a tissue-penetrating stylet sized to be received in the lumen of the cannula.

Further examples of the disclosed technology can have one or more alternative or additional features. The microwave ablation system can include a fixation mechanism for fixing a location of the cannula within patient tissue. In some examples, the window portion of the cannula overlaps the radiating portion of the microwave ablation probe at the distal portion of the probe body. In some examples, the system also includes a connector that fixes a position of the microwave ablation probe in relation to the cannula when the microwave ablation probe is inserted in the lumen of the cannula. In some examples, the connector fixes the radiating portion of the microwave ablation probe in a position adjacent to the window portion of the cannula. In some examples, the window portion comprises a non-metallic material. In some examples, the non-metallic material is a dielectric polymer.

Other examples of the disclosed technology include a microwave ablation method that includes the steps of inserting a microwave ablation probe into a lumen of a cannula, aligning a radiating portion of the microwave ablation probe with a portion of the cannula that is at least partially transparent to microwave energy, and causing microwave energy to be emitted from the radiating portion of the microwave ablation probe. Alternatively or in addition, the method includes inserting a tissue-piercing stylet into a lumen of the cannula. Alternatively or in addition, the method includes piercing a body of tissue with the stylet while the stylet is inserted in the cannula lumen and removing the stylet from the cannula lumen. Alternatively or in addition, the method includes fixing the cannula at a location in the body of tissue and removing the stylet from the cannula lumen while the cannula is fixed at the location in the tissue. Alternatively or in addition, the method includes ablating the tissue with microwave energy emitted from the radiating portion of the microwave ablation probe.

Further examples of the disclosed technology can have one or more alternative or additional features. In some examples, the method includes removing a biopsy sample of the tissue through the cannula lumen. In some examples, the method includes cooling the microwave ablation probe. In some examples, the method includes fixing the microwave ablation probe to the cannula using a connector.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense.

Figure 1:
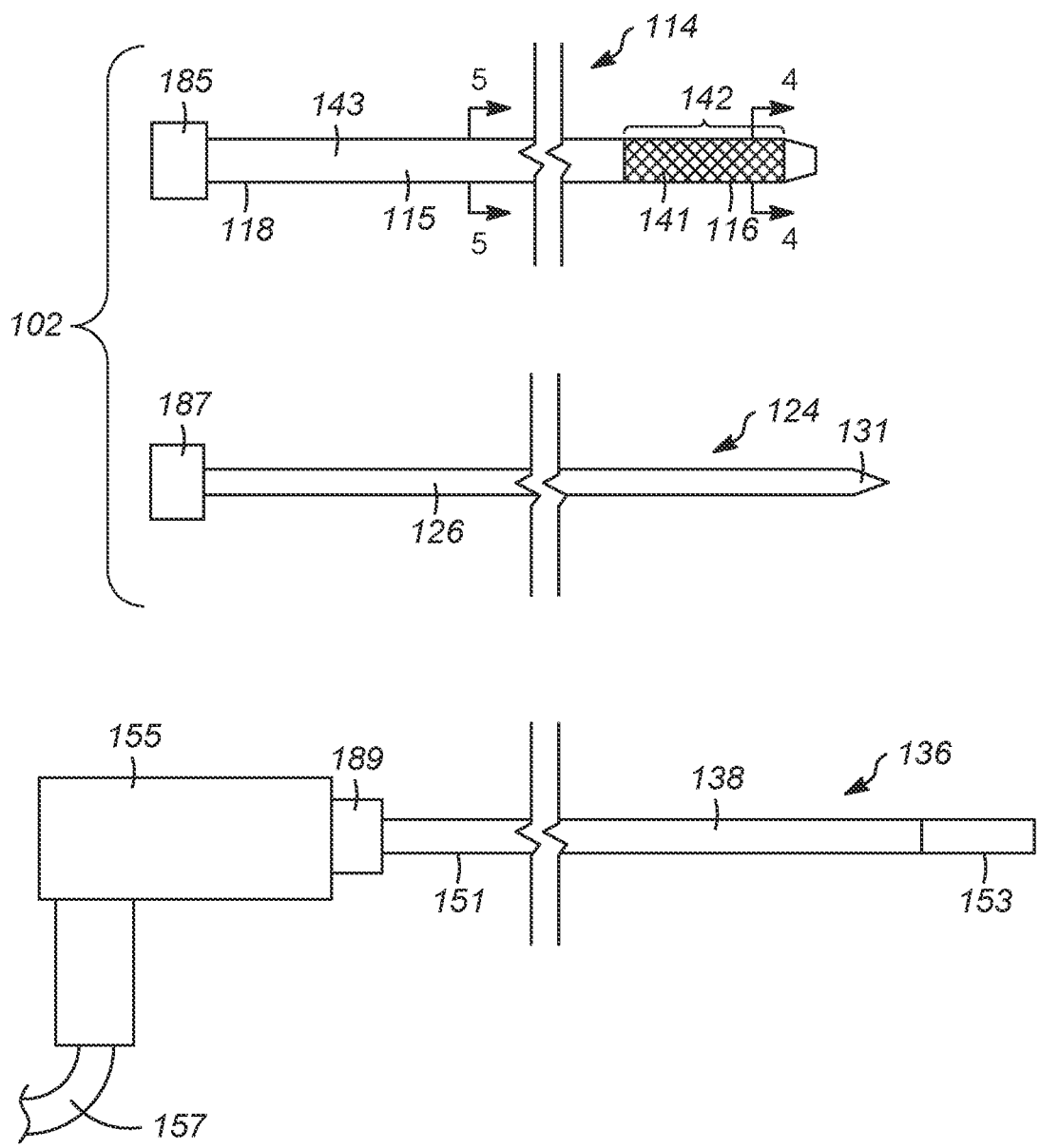
FIG. 1 is a side view of a microwave ablation system including an introducer set and a microwave ablation probe according to some examples.

Unless indicated, the figures are not drawn to scale. While examples herein are susceptible to various modifications and alternative forms, specifics thereof have been shown by way of examples and drawings, and will be described in detail. It should be understood, however, that the scope herein is not limited to the particular examples described. On the contrary, the intention is to cover modifications, equivalents, and alternatives falling within the spirit and scope herein.

DETAILED DESCRIPTION

The present technology provides an introducer set for a microwave ablation probe. In some examples, the introducer set includes a cannula with a lumen, and a stylet configured to be inserted in the lumen. The stylet of the introducer set has a tissue-piercing or tissue-penetrating tip that is used to pierce patient tissue and direct the introducer set to the desired location for ablation. Once the introducer set is positioned, the stylet can be removed from the lumen of the cannula. A microwave ablation probe is inserted into the lumen of the cannula to provide microwave ablation therapy.

The cannula of the introducer set is provided with a cannula body, and a portion of the cannula body is transparent to microwave radiation. In some examples, the cannula body includes a window portion made of a material through which microwave energy can pass. In some examples, the cannula body has at least one segment constructed of a material that is transparent to microwave radiation and at least one segment constructed of a material that is not transparent to microwave radiation. In some examples, the window portion of the cannula is constructed at least partially from a non-metal material. In some examples, the cannula body is constructed partially from a non-metal material and partially from a metal material. In some examples, the cannula body is made entirely from a non-metal material.

During use, the stylet is inserted into the lumen of the cannula. The stylet and cannula of the introducer set are then inserted into patient tissue and guided to the desired location for ablation. The introducer set pierces the patient tissue, allowing the cannula to travel through the tissue to the ablation location. The stylet has the tissue-piercing tip. The microwave-transparent window portion of the cannula body is placed adjacent to the tissue to be ablated.

In some examples, the cannula is secured at the desired location using a fixation mechanism. The fixation mechanism prevents the cannula from changing its location in the tissue. The stylet is then removed, leaving the cannula in place in the patient tissue.

A microwave ablation probe is inserted into the cannula lumen. The microwave ablation probe has a radiating portion that emits microwave radiation. The radiating portion of the microwave ablation probe aligns with the microwave transparent or non-metal portion of the cannula body. Microwave radiation emitted from the radiating portion travels through the microwave-transparent or non-metal material of the cannula from the inside of the cannula to outside of the cannula and into patient tissue, where the microwave energy heats the patient tissue and destroys the diseased cells. The use of an introducer set with a cannula with a microwave transparent window allows the microwave ablation probe to be fully housed within the cannula.

The use of an introducer set having a tissue-piercing stylet reduces the requirements for strength, rigidity, and maneuverability of the microwave ablation probe. In some past systems, a ceramic trocar tip of the microwave ablation probe is used to pierce tissue and maneuver through tissue to the ablation site, and there is no introducer set used with the microwave ablation probe. In the systems described herein, the stylet of the introducer set will be used to puncture the patient tissue and maneuver to the ablation site. As a result, it is possible to use a microwave ablation probe with fewer mechanical requirements, reduced rigidity requirements, reduced maneuverability requirements, and having a smaller diameter compared to prior systems. Also, a tissue-piercing tip provided on the stylet, which can be metal in some examples, can be made less expensively than a ceramic trocar tip provided on past microwave ablation probe.

Because the introducer set of the present technology is introduced into the body independently of the microwave ablation probe and does not need to have all the elements of a microwave ablation probe, the introducer set can be made to have better mechanical strength and a reduced cost compared to past microwave ablation probes. Also, in some examples, the outer diameter of the introducer set which can accommodate the microwave ablation probe, is less than the outer diameter of past microwave ablation probes that are used without introducer sets.

A metal tissue-piercing tip on the stylet can be more easily observed in some imaging systems than the ceramic tip of past microwave ablation probes, facilitating better visualization under ultrasound and fluoroscopy. The increased visualization can facilitate multiple probe placement during ablation of multiple sites.

The cannula of the introducer set can be used for many other purposes. A biopsy needle can be inserted into the cannula before the ablation procedure, after the ablation procedure, or both to collect tissue samples. A drug delivery catheter can be inserted into the cannula before the ablation procedure, after the ablation procedure, or both to deliver drug therapy.

In some examples, a navigational device is provided, such as a navigational marker or a navigational sensor. One example of a navigational sensor is as an electromagnetic navigational sensor. The navigational device can be located in or on the cannula, or it can be located in or on the stylet. The navigational device is used to ensure that the window portion of the cannula—and thus the radiating portion of the microwave ablation probe, which is aligned with the window portion—is in the correct location for ablation. If the navigational device is provided in the stylet, the location of the stylet is known, and the location of the cannula can be computed based on the known spatial relation between the stylet and the cannula. If the navigational system is provided in or on the cannula, the location of the window portion of the cannula can also be determined.

More than one introducer set and microwave ablation probe can be used simultaneously to provide ablation to multiple sites. Alternatively, the microwave ablation probe can be repositioned to a different location to apply microwave ablation therapy to the new location. This may be done by removing the probe from the cannula, reinserting the stylet into the cannula, and repositioning the introducer set to the different location. Then, the stylet can be removed and the microwave ablation probe can be reinserted to apply microwave ablation therapy to the different location. This sequence can be repeated for additional therapy locations.

Introducer Set for a Microwave Ablation Probe

Figure 2:
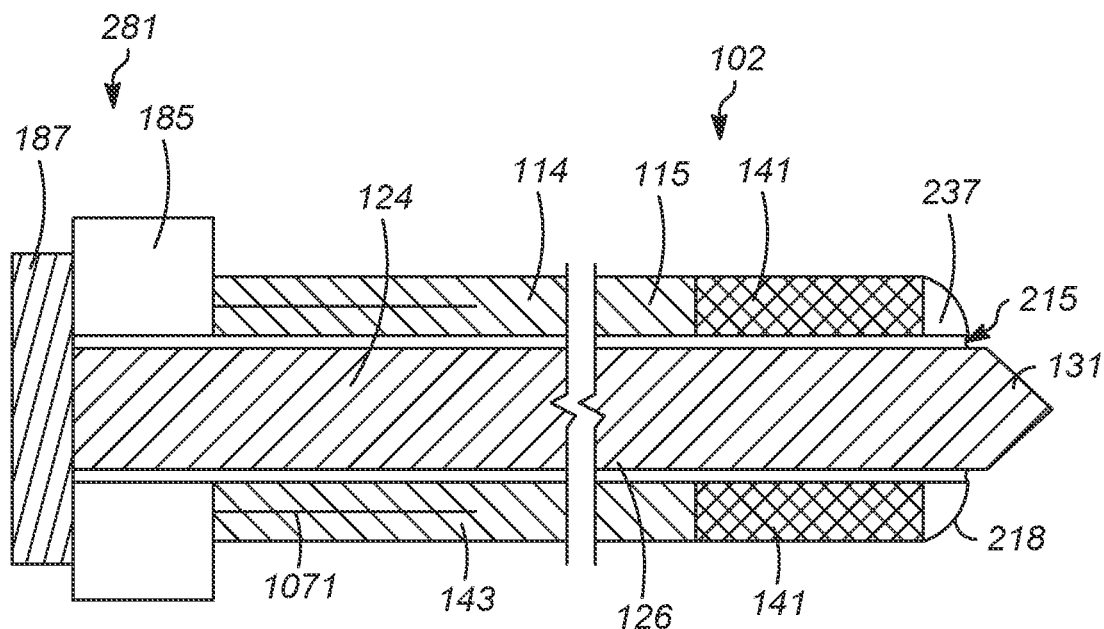
FIG. 2 is a cross-sectional view of an introducer set according to some examples.
Figure 3:
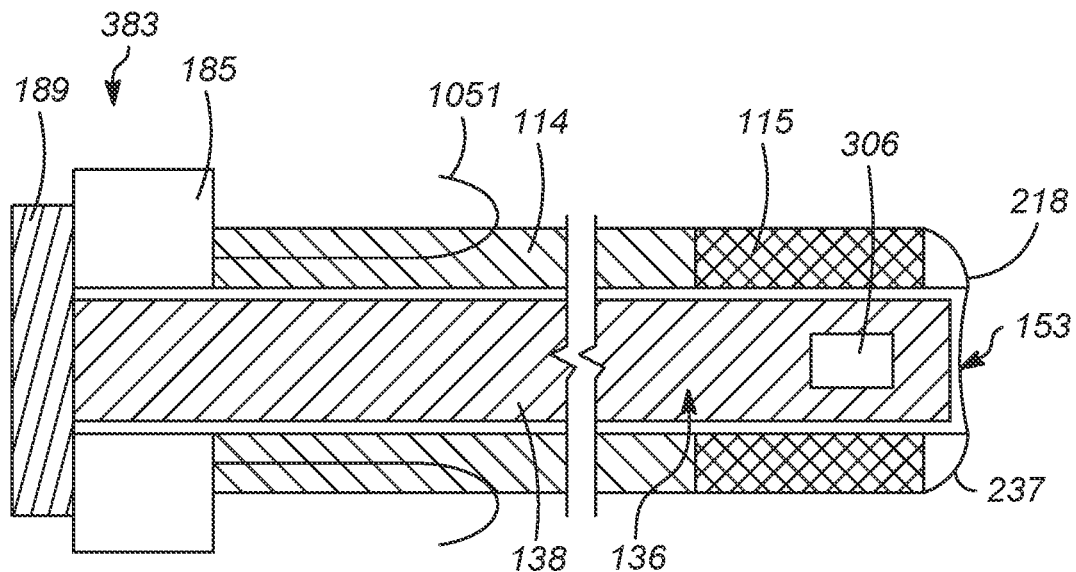
FIG. 3 is a cross-sectional view of the microwave ablation probe in combination with a cannula of an introducer set.

FIG. 1 shows a side view of a microwave ablation system according to some examples that includes an introducer set and a microwave ablation probe. The introducer set 102 includes a cannula 114 and a stylet 124. The introducer set 102 is configured to be used with a microwave ablation probe 136. FIG. 2 is a cross-sectional view of the introducer set 102 and FIG. 3 is a cross-sectional view of the microwave ablation probe 136 in combination with the cannula 114 of the introducer set 102.

The cannula 114 has a lumen 215 (shown in FIGS. 2-3) extending through the middle of the cannula 114 from a distal portion 116 to a proximal portion 118 of the cannula 114. In some examples, the cannula 114 has a blunt tip. The blunt tip is not configured to pierce tissue. In some examples, including the example of FIG. 1, the cannula body 115 has a non-metal portion 141 and a metal portion 143. In the example of FIG. 1, the non-metal portion 141 is situated near the distal portion 116, and the metal portion 143 is situated near the proximal portion 118. In some examples, the non-metal portion 141 of the cannula 114 is a window portion 142 that is at least partially transparent to microwave energy; that is, radiation emitted in the microwave range of the electromagnetic spectrum with a frequency on the order of about 300 megahertz to 300 gigahertz. In some examples, the non-metal portion 141 is at least partially transparent to microwaves having a frequency of about 915 megahertz, about 2.45 gigahertz, or both. Microwave radiation emitted by a radiation source inside of the lumen 215 of the cannula 114 will pass through the transparent non-metal portion 141 of the cannula 114.

In some examples, the non-metal portion 141 is transparent to electromagnetic radiation in one or more other regions of the electromagnetic spectrum, e.g., visible light (about $4 \times 10^{14}$ Hz to $8 \times 10^{14}$ Hz), x-rays (about $3 \times 10^{16}$ Hz to $3 \times 10^{19}$ Hz), etc. In some examples the non-metal portion is not transparent to one or more other regions of the electromagnetic spectrum.

The stylet 124 has a stylet body 126 with a tissue-penetrating stylet tip 131. In the example of FIG. 1, the stylet 124 has a solid trocar tip. As used herein, the term trocar means a three-sided cutting tip. The stylet 124 has an outside diameter that is smaller than a diameter of the lumen 215 of the cannula 114. This allows the stylet 124 to be inserted into the lumen 215, as shown in FIG. 2. The stylet can be made of metal, such as stainless steel. In some examples, the cannula 114 is less rigid than the stylet 124. The rigidity of the stylet 124 affects the overall rigidity of the introducer set 102.

The microwave ablation probe 136 has an elongated probe body 138 with a proximal end 151 and a distal end 153. A handle 155 and a power coupling 157 are also provided. In some examples, the elongated probe body 138 comprises a blunt tip that is not configured to penetrate tissue.

Inside of the probe body 138 is a radiating portion 306 that emits microwave energy. In some examples, the radiating portion 306 is a microwave antenna, which can be a helical antenna. A microwave antenna can be a monopole antenna, dipole antenna, or other configuration. The microwave ablation probe 136 may utilize a coaxial antenna. The microwave ablation probe 136 can include a cooling system (not shown) to prevent excess heating along the length of the probe body 138. The microwave ablation probe 136 can include a choke (not shown) to limit the microwave radiation field. The elongated probe body 138 has an outside diameter that is smaller than the diameter of the lumen 215, allowing the microwave ablation probe 136 to be inserted into the lumen 215, as shown in FIG. 3.

Turning to FIG. 2, the cannula 114 has a lumen 215 sized to receive the stylet body 126 of the stylet 124. The stylet 124 can be slidably inserted into the lumen 215 of the cannula 114, and can also be slidably removed from the lumen 215. In some examples, a cannula-stylet connector 281 locks the stylet 124 in place in relation to the cannula 114 so that the stylet 124 and cannula 114 do not separate during insertion into patient tissue. When locked together, the stylet tip 131 protrudes from a distal end 218 of the cannula body 115. This allows the stylet tip 131 to pierce and penetrate the patient tissue.

Turning to FIG. 3, the lumen 215 is sized to receive the elongated probe body 138 of the microwave ablation probe 136. The microwave ablation probe 136 can be slidably inserted into the lumen 215 of the cannula 114, and can also be slidably removed from the lumen 215. In some examples, a cannula-ablation probe connector 383 fixes the position of the microwave ablation probe 136 in relation to the cannula 114 when the microwave ablation probe 136 is inserted in the lumen 215 of the cannula 114. This way the microwave ablation probe 136 does not move relative to the cannula 114 during ablation. In some examples, including the example of FIG. 3, when connected using the cannula-ablation probe connector 383, the distal end 153 of the probe body 138 does not protrude from the distal end 218 of the cannula body 115.

In the example of FIG. 3, the non-metal portion 141 of the cannula body 115 overlaps the radiating portion 306 of the microwave ablation probe 136 when the probe body 138 is inserted into the cannula 114. That is, at least a portion of the electromagnetic radiation emitting from the radiating portion 306 will be incident on the window portion 142 of the cannula body 115. Because the window portion 142 is transparent to microwave radiation, the radiation will pass through the cannula body 115 unimpeded, without being absorbed or reflected by the cannula body 115.

The length of the window portion 142 of the cannula body 115 is based on the particular antenna used in the microwave ablation probe 136. In some examples, the length is at least about 7 millimeters, at least about 10 millimeters, or at least about 13 millimeters. In some examples, the length is at most about 30 millimeters, or at most about 20 millimeters. In one example, the length is about 15 millimeters. A longer radiating portion 306 requires a longer length of the cannula body 115 to be transparent, thus requiring a longer window portion 142. A radiating portion that is shorter in length can accommodate a shorter length of the window portion 142. The window portion 142 is positioned along the length of the cannula body 115 such that when the radiating portion 306 emits microwave energy, at least a portion of the microwave energy will encounter the window portion 142 and pass through the window portion 142 so that surrounding tissue can be ablated.

Figure 4:
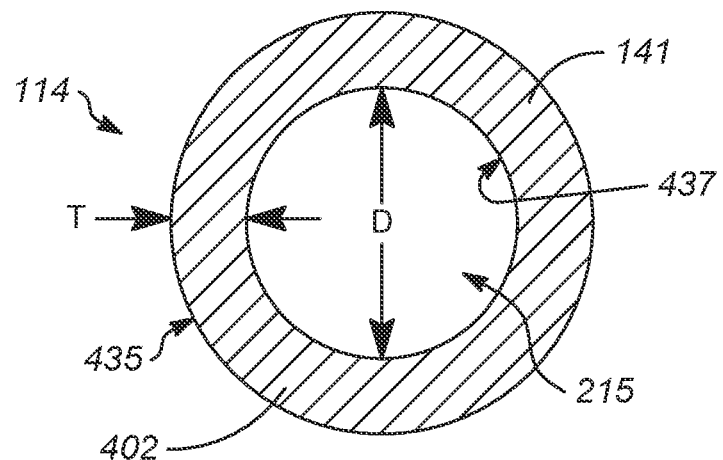
FIG. 4 is a cross sectional view of the cannula of FIG. 1 taken along the line 4-4.

In some examples, the outer diameter of the cannula is at least about 16 gauge (1.29 millimeters), at least about 15 gauge (1.45 millimeters), or at least about 14 gauge (1.63 millimeters). In some examples, the outer diameter of the cannula is at most about 12 gauge (2.05 millimeters), or at most about 13 gauge (1.83 millimeters). In some examples, the inner diameter D of the cannula, shown in FIG. 4, is at least about 18 gauge (1.02 millimeters), at least about 17 gauge (1.15 millimeters), or at least about 16 gauge (1.29 millimeters). In some examples, the inner diameter D of the cannula is at most about 13 gauge (1.83 millimeters) or at most about 14 gauge (1.63 millimeters).

The microwave ablation probe and the stylet are sized to easily fit within and slide within the lumen of the cannula. The outer diameter of the microwave ablation probe and the outer diameter of the stylet are less than the inner diameter of the cannula. In some examples, the outer diameter of the microwave ablation probe is at least about 18 gauge (1.02 millimeters), at least about 17 gauge (1.15 millimeters), or at least about 16 gauge (1.29 millimeters). In some examples, the outer diameter of the microwave ablation probe is at most about 12 gauge (2.01 millimeters), at most about 13 gauge (1.83 millimeters), or at most about 14 gauge (1.63 millimeters). In some examples, the outer diameter of the stylet is at least about 18 gauge (1.02 millimeters), at least about 17 gauge (1.15 millimeters), or at least about 16 gauge (1.29 millimeters). In some examples, the outer diameter of the stylet is at most about 12 gauge (2.01 millimeters), at most about 13 gauge (1.83 millimeters), or at most about 14 gauge (1.63 millimeters).

The cannula, stylet and microwave ablation probe can be provided in a variety of lengths and are elongate in shape. The length of each of these components is much larger than its diameter. For example, the length may be 10 times the diameter or more, 50 times the diameter or more, 100 times the diameter or more, or 200 times the diameter or more. The length may be at least 5 centimeters or at least 10 centimeters, in some examples.

Locking Mechanisms Between Cannula and Stylet or Microwave Ablation Probe

Some implementations of the disclosed technology can include a cannula-stylet connector 281 and a cannula-ablation probe connector 383. In some examples, the cannula 114 includes a cannula connector 185 that is configured to lock the cannula 114 in place with respect to either the stylet 124 or the microwave ablation probe 136 or both. A stylet connector 187 of the stylet 124 interfaces with the cannula connector 185 to lock the cannula body 115 in place with respect to the stylet body 126. In some examples, such as that of FIG. 2, when the cannula connector 185 and the stylet connector 187 are locked together, the spatial relationship between the cannula body 115 and the stylet body 126 is fixed such that the stylet tip 131 protrudes from the distal end 218 of the cannula body 115. The cannula-stylet connector 281 can include, for example, a Luer Lock fitting, or other similar mechanism.

In the example of FIG. 3, the microwave ablation probe 136 has a probe connector 189 that is configured to lock the probe body 138 in place with respect to the cannula body 115. The probe connector 189 interfaces with the cannula connector 185 to lock the probe body 138 in place with respect to the cannula body 115. In some examples, such as that of FIG. 3, when the cannula connector 185 and the probe connector 189 are locked together, the spatial relationship between the probe body 138 and the cannula body 115 is fixed such that the radiating portion 306 of the microwave ablation probe 136 does not protrude from the distal end 218 of the cannula body 115. The cannula-ablation probe connector 383 can include, for example, a Luer Lock fitting, or other similar mechanism.

It will be appreciated that the cannula-stylet connector 281 and the cannula-ablation probe connector 383 can be implemented in a number of different ways, and the particular example provided here is not limiting.

Materials for Cannula

FIG. 4 shows a cross-section of the non-metal portion 141 of the cannula body 115 along line 4-4 of FIG. 1. The non-metal portion 141 of the cannula body 115 has an outer surface 435. The lumen 215 has an inner surface 437 defining a lumen diameter D. In some examples, the non-metal portion 141 is made of a non-metal material throughout the thickness T of the cannula wall 402 from the inner surface 437 to the outer surface 435. The non-metal portion 141 is transparent to microwave radiation. In some examples, the non-metallic material is a dielectric polymer. In some examples, the non-metal portion 141 is made of a braided material. The non-metal portion 141 of the cannula body 115 can be a strengthened polymer tube such as polyimide tubing with an embedded braid or coil, such as an embedded polymer braid or coil.

In some examples, the probe is less rigid than the cannula. In some examples, the probe has a flexural modulus that is less than or equal to the cannula. This relationship facilitates the cannula guiding the probe to the ablation location as the probe is inserted into the cannula without the probe causing the position of the cannula to shift. In other examples, the cannula is less rigid than the probe.

Material examples for a polymer tube of the non-metal portion of the cannula body 115 include fluoropolymers, urethanes, polyether block amides (PEBA), polypropylene, polyethylene, polyamide (nylon), polyimide, polyetherimide (PEI), polysulfone, and polyetheretherketone (PEEK). Material examples for a polymer fiber braid or coil include polyamides, polyester, and aramids. Alternatively, the non-metal portion 141 can be a ceramic material.

Additional options for the material of an embedded braid or coil include aromatic polyester fiber, para-aramid synthetic fiber, carbon fiber, fiber spun from liquid-crystal polymer, poly-paraphenylene terephthalamide fiber, VECTRAN™ material fiber, available from Kuraray Co., Ltd., with a place of business in Kurashiki, Okayama, Japan, and KEVLAR™ material fiber, available from DowDuPont Inc., with a place of business in Willington, Del. A VECTRAN™ material liquid-crystal polymer braid is transparent to microwave energy, and has a high dielectric strength. In some examples, the non-metal portion 141 is resilient at high temperatures, for example having a melt temperature of greater than 150 degrees Celsius.

Figure 5:
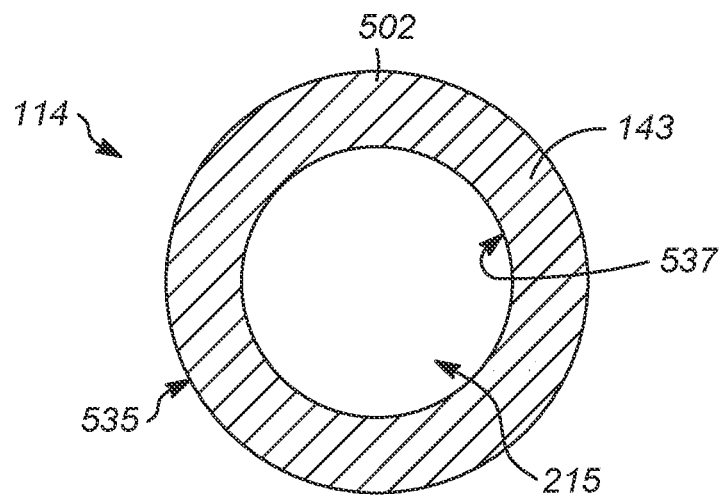
FIG. 5 is a cross-sectional view of the cannula of FIG. 1 taken along the line 5-5.

FIG. 5 shows a cross-section of the metal portion 143 of the cannula body 115 along the line 5-5 of FIG. 1. The metal portion 143 of the cannula body 115 has an outer surface 535. Along this portion of the body, the lumen 215 has an inner surface 537. In some examples, the metal portion 143 is made of a metal material throughout the thickness of the cannula wall 502 from the inner surface 537 to the outer surface 535. In some examples, the metal portion 143 of the cannula body 115 can comprise stainless steel. In some examples, the metal-containing region can comprise nitinol or a polymer tubing with an embedded metal braiding such as stainless steel or tungsten braiding.

Alternative Cannula Examples

Figure 6:
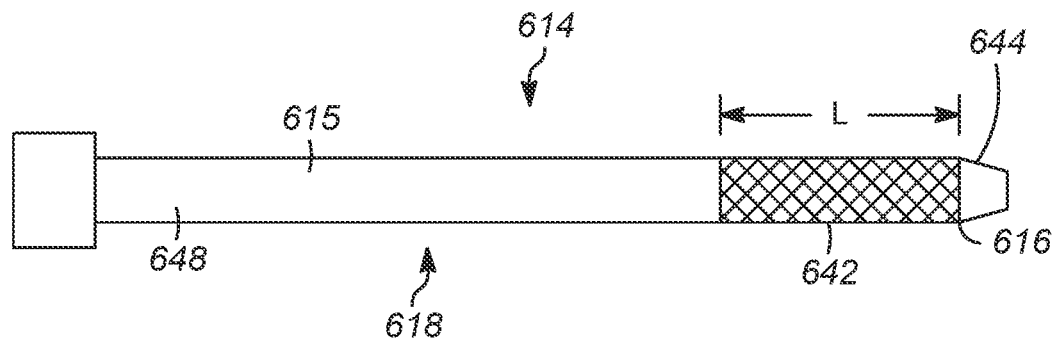
FIG. 6 is a side view of an alternative example of a cannula for an introducer set.
Figure 7:
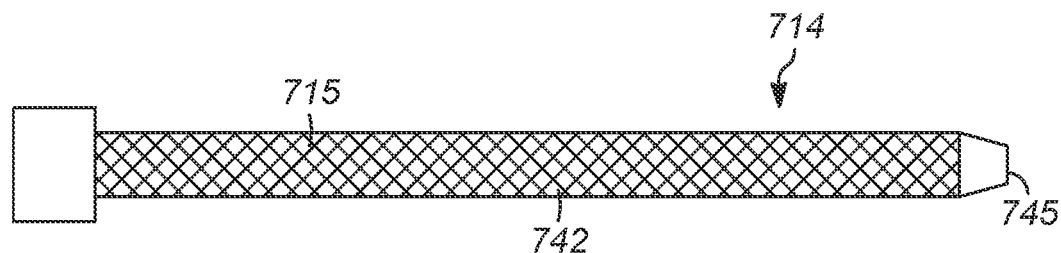
FIG. 7 is a side view of a second alternative example of a cannula for an introducer set.

FIGS. 6 and 7 show alternative examples of a cannula for an introducer set for a microwave ablation probe. In the example of FIG. 6, the cannula 614 has a cannula body 615 with a first metal portion 648 at a proximal end 618, a second metal portion 644 at a distal end 616 of the cannula body 615, and a non-metal portion 642 extending between the first metal portion 648 and the second metal portion 644. Like the cannula 114 of FIG. 1, the cannula 614 has a lumen (not seen in FIG. 6) sized to receive a stylet. The length L of the non-metal portion 642 will be determined based on the particular antenna used in the microwave ablation probe.

The non-metal portion 642 is made of a non-metal material throughout the thickness of the cannula wall from the inner surface of the lumen to the outer surface of the cannula body 615. The first metal portion 648 and the second metal portion 644 can be made of a metal material throughout the thickness of the cannula wall from the inner surface of the lumen to the outer surface of the cannula body 615.

In the example of FIG. 7, the cannula 714 has a cannula body 715 that substantially comprises a non-metal portion 742. In this example, the cannula body 715 does not contain a metal portion. Like the cannula 114 of FIG. 1, the cannula 714 has a lumen (not seen in FIG. 7) sized to receive a stylet. The non-metal portion 742 is made of a non-metal material throughout the thickness of the cannula wall from the inner surface of the lumen to the outer surface of the cannula body 715. A navigational device 745 is disposed in the lumen of the cannula 714 at the tip. As will be described in more detail below, the navigational device 745 is used to locate and/or track the position of the cannula 114 inside patient tissue.

Alternative Example of a Stylet for an Introducer Set

Figure 8:
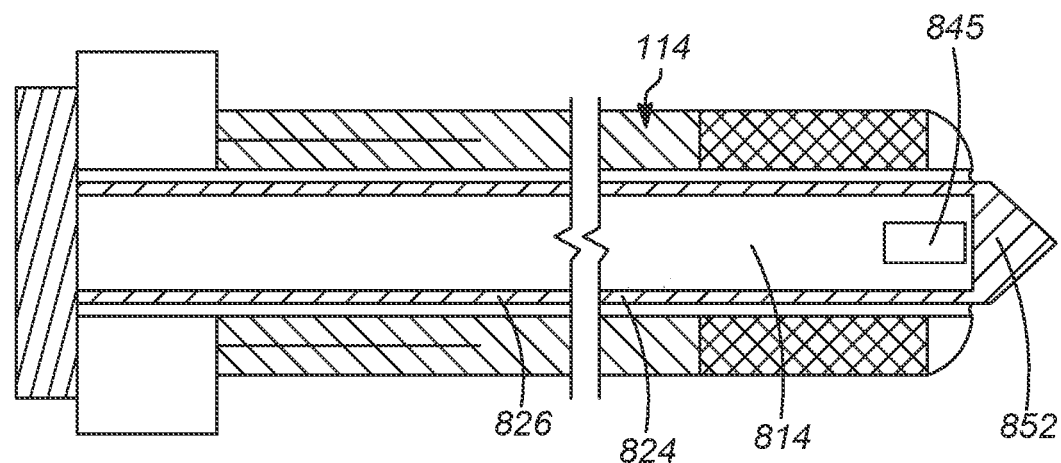
FIG. 8 is a cross-sectional view of an alternative example of a stylet for an introducer set within a cannula.

FIG. 8 shows an alternative example of a stylet for an introducer set for a microwave ablation probe. In the example of FIGS. 1 and 2, the stylet 124 is a solid piece. In the example of FIG. 8, the stylet 824 has a stylet body 826 with a lumen 814 running through the stylet body 826. The stylet 824 has a tissue-piercing tip 852. The stylet tip 852 can be a trocar. A navigational device 845 is disposed inside the lumen 814 of the stylet 824. As will be described in more detail below, the navigational device 845 is used to locate and/or track the position of the cannula 114 inside patient tissue.

Navigational Devices and Systems

Some examples of the disclosed technology provide a navigation device for use with a navigation system for locating the position of the introducer set 102, the microwave ablation probe 136, or both inside of a patient's body. The navigation device can be at least one navigational marker or at least one navigational sensor provided on one or more of the cannula of the introducer set, the stylet of the introducer set, and the microwave ablation probe 136.

As the term is used herein, a navigational marker can be, for example, a physical characteristic of the introducer set that is visible using fluoroscopy, ultrasound imaging, computed tomography (CT) imaging or other medical imaging techniques. The navigational marker may be made of a material, such as metal, that is visible under one or more medical imaging techniques.

As the term is used herein, a navigational sensor is similar to a navigational marker in that it also is visible using one or more medical imaging techniques. In addition, a navigational sensor is capable of communicating information about the body tissue where it is located to an external device that is part of the navigation system. A navigational sensor can be an electromagnetic navigation sensor, for example. Electromagnetic navigation systems are used to locate the position of a medical tool within a patient's body using a magnetic field, an electric field, or both. Data, such as impedance and electrical potential measurements, can be transmitted from the electromagnetic navigation sensor within the body to an external receiver. In some examples, electromagnetic navigation sensors decrease or remove the need to perform fluoroscopy to locate the medical tool within the patient. Examples of electromagnetic navigation systems and tools include RHYTHMIA HDx™ Mapping System, INTELLANAV™ ablation catheters, and INTEL-LAMAP ORION™ mapping catheters available from Boston Scientific Corporation Inc., having a place of business in Natick, Mass. Another example of a navigational system is superDimension™ navigation system available from Medtronic having a place of business in Minneapolis, Minn. Other examples of navigational systems and instruments are SPiN Thoracic Navigation System™ and Always-On Tip Tracked™ Instruments available from Veran Medical Technologies having a place of business in St. Louis, Mo.

Now referring to FIGS. 2-3, in some examples of the disclosed technology, the cannula 114 includes at least one navigational device 237. The navigational device 237 can be located at the distal end 218 of the cannula 114. In some examples, the navigational device 237 is located at the extreme distal end or distal tip of the cannula 114. In alternative examples, the navigational device 237 can be located at a different portion of the cannula 114.

In some examples of the disclosed technology, the stylet 124 of FIGS. 1-3 includes at least one navigational device (not shown). In some examples, the stylet body 126 has echogenic features that are visible during ultrasound imaging. In other examples, the stylet body 126 does not include a navigational device.

In the cannula example of FIG. 7 having a non-metal cannula body portion 742, the cannula 714 can include at least one navigational device 745, which can be a navigational marker or a navigational sensor. The cannula 714 can be used with a stylet having a navigational device or can be used with a stylet lacking a navigational device. The cannula 714 can be used with a microwave ablation probe having a navigational device or can be used with a microwave ablation probe lacking a navigational device.

In the introducer set example of FIG. 8 having a stylet 824 defining a lumen 814, a navigational device 845 is disposed inside the lumen 814 of the stylet 824 and is positioned near a distal end of the stylet 824. The navigational device 845 can be a navigational marker or a navigational sensor. The stylet 824 having a navigational device 845 can be used with a cannula that also includes a navigational device or can be used with a cannula that does not include a navigational device.

A microwave ablation probe can include a navigational device such as a navigational marker or navigational sensor, in various examples.

Fixation Mechanism

In some examples of the disclosed technology, a fixation mechanism is provided for fixing the location of the introducer set and microwave ablation probe in relation to patient tissue. When a fixation mechanism is employed, the cannula 114 is fixed in place in relation to patient tissue such that the cannula 114 does not move with respect to the patient tissue when the stylet 124 or microwave ablation probe 136 are inserted into or removed from the lumen of the cannula 114. Fixing the cannula 114 in place in relation to patient tissue prevents the cannula 114 from changing its location inside the body. This ensures that the cannula 114 is in the desired location in relation to the tissue to be ablated. In some examples, the fixation mechanism itself also does not move in relation to patient tissue after the cannula has been steered to the desired location and fixed in patient tissue.

Figure 9:
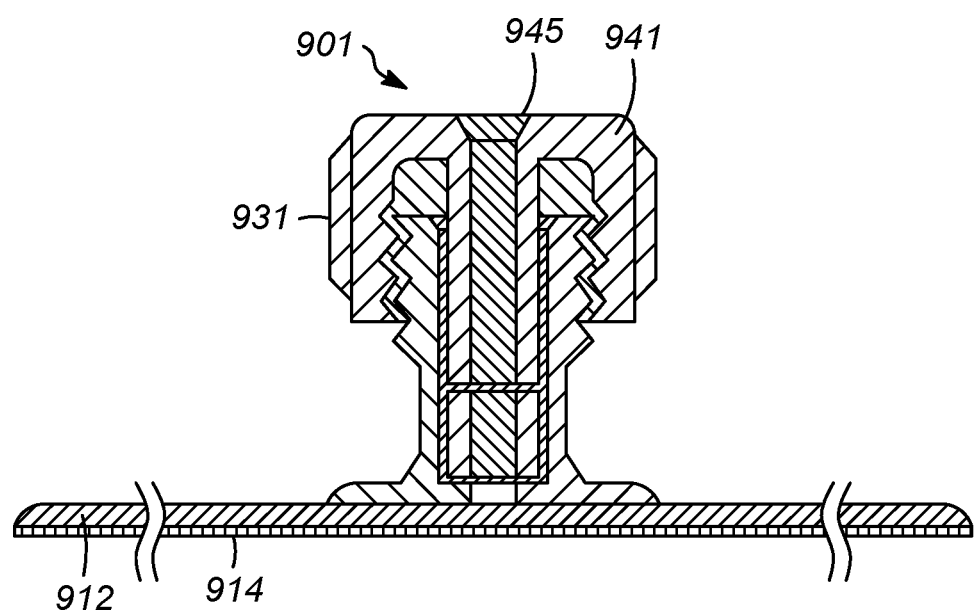
FIG. 9 is a cross-sectional view of a fixation mechanism for an introducer set according to some examples.

FIG. 9 is a cross-sectional view of a fixation mechanism 901 for an introducer set according to some examples. A self-adhesive pad 912 includes a layer of adhesive 914 configured to adhere to patient skin. An adapter 931 is connected to the self-adhesive pad 912. The adapter 931 is configured to provide a passage for the introducer set 102 and microwave ablation probe 136 to enter the patient's body. In the example of FIG. 9, the adapter 931 is a Tuohy Borst adapter. The adapter 931 has an adapter body 921 and a threaded cap 941. A central passage 945 is provided for the introducer set 102 to enter the patient's body. A locking grommet allows the introducer set 102 to be locked in place with respect to the fixation mechanism 901. During use, the introducer set 102 is inserted into the central passage 945. The cannula 114 is then locked in place in relation to the fixation mechanism 901. This fixes the location of the cannula 114 in the patient tissue at the location to be ablated.

Figure 10:
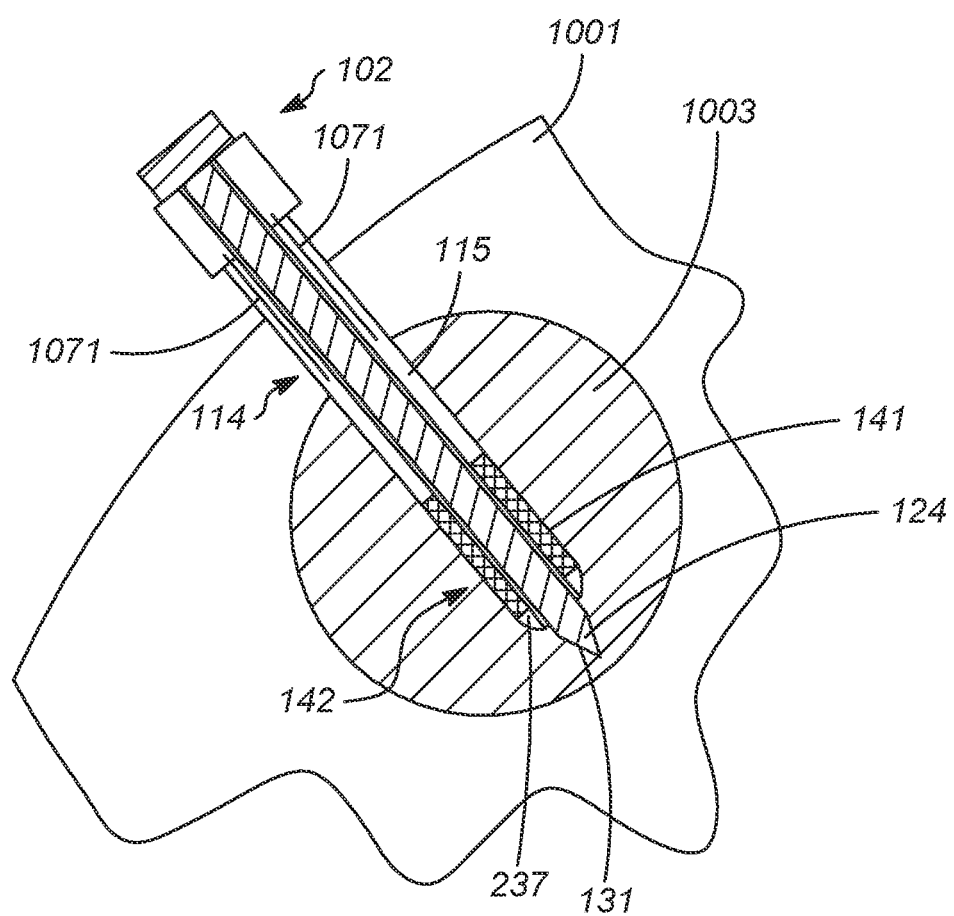
FIG. 10 is a cross-sectional view of the introducer set of FIG. 1 inserted into patient tissue.
Figure 11:
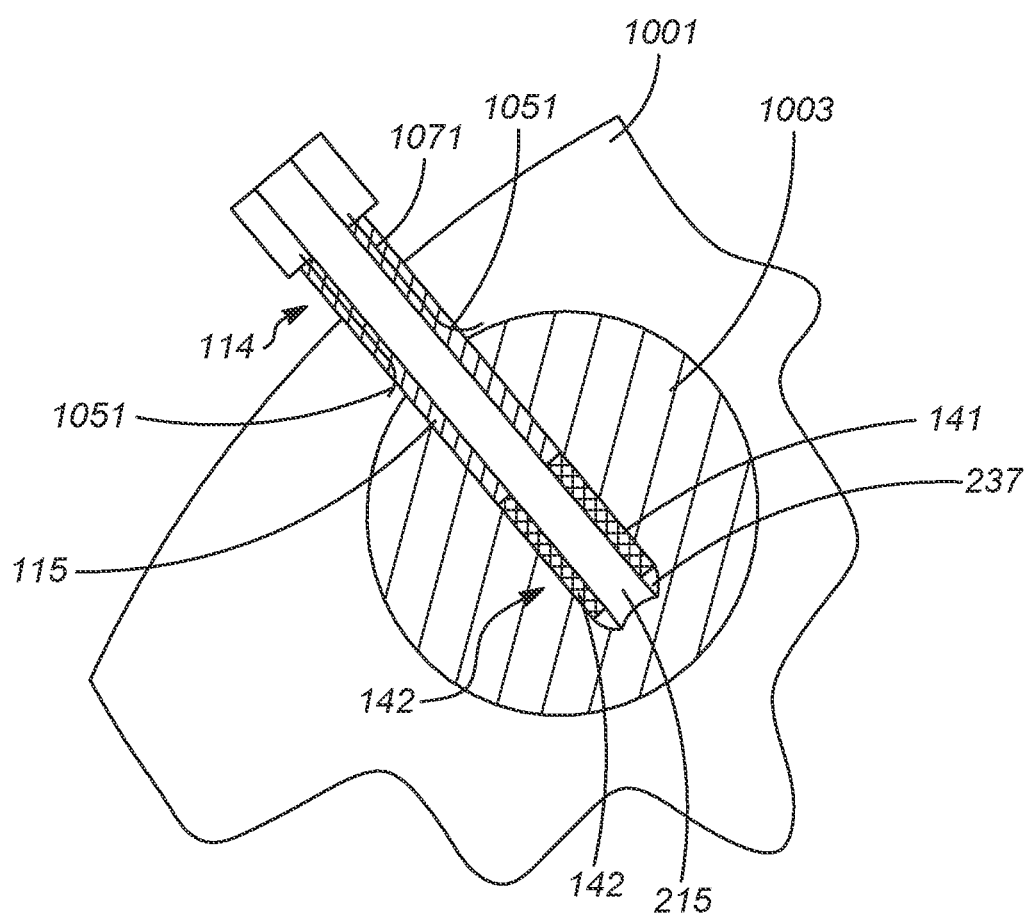
FIG. 11 is a cross-sectional view of the cannula of FIG. 1 fixed in patient tissue.

Turning to FIGS. 10 and 11, in an alternative example of a fixation mechanism, the cannula 114 has a plurality of tines 1071. The tines each have a distal tip 1051 capable of piercing patient tissue. The tines 1071 can travel through the pierced tissue. In some examples, the tines 1071 can extend through the cannula body 115. When the introducer set 102 is inserted into patient tissue 1001 and into tissue 1003 to be ablated, such as a tumor, the tines initially are retracted, as demonstrated in FIG. 10. When the introducer set 102 reaches the desired location for ablation, the tines 1071 are deployed, as demonstrated in FIG. 11. The deployed tines pierce patient tissue and travel through the patient tissue. The deployed tines fix the location of the cannula 114 in the patient tissue at the location to be ablated. In some examples, the deployed tines fix the location of the cannula 114 by curving outward and upward against the direction of insertion of the cannula 114. In some examples, tines are present and can be deployed at multiple locations along the length of the shaft of the cannula.

Alternative fixation mechanisms are contemplated. For example, a suture attachment could be used to fix the location of an exterior portion of the cannula 114 to the patient's skin, so that the tip of the cannula stays within the patient tissue at the location to be ablated. Alternatively, a suction pad device could be secured to an exterior portion of the cannula 114 to the patient's skin using negative pressure, to provide fixation of the tip of the cannula in relation to the location to be ablated. Other fixation mechanisms are possible and are within the scope of the current claims.

Method of Using an Introducer Set with a Microwave Ablation Probe

A method is provided for introducing and ablating with a microwave ablation probe. FIG. 10 is a cross-sectional view of the introducer set of FIG. 1 inserted into patient tissue. The method includes inserting a tissue-piercing stylet 124 into a lumen 215 of a cannula 114, to form an introducer set 102. The method further includes piercing a body of tissue 1001 with the stylet tip 131 while the stylet 124 is inserted in the cannula 114 lumen 215. The introducer set 102 is moved through patient tissue 1001 until the cannula 114 is located at a tissue portion 1003 to be ablated, such as a tumor. In some examples, the transparent window portion 142 is situated in the location of the tissue to be ablated. In some examples the cannula 114 is fixed at this location in the tissue 1001. In alternative examples, it is possible that the cannula 114 is not fixed at this location in the tissue 1001.

In some examples, while the introducer set 102 travels through the patient tissue, and/or when the cannula 114 is at the location of the tissue to be ablated, a navigational system is employed. The navigational system can include a navigational device such as a navigational marker or a navigational sensor, a field or radiation source, and a detector of an electrical field, magnetic field, electromagnetic radiation, or a similar system.

As one example, a navigational device 237 on the cannula 114 can be employed. While the cannula 114 is inside of patient tissue, one or more imaging scans are performed of the cannula 114 and the tissue 1003 to be ablated. The navigational device 237 of the cannula 114 is present in patient tissue 1001 at the location of tissue 1003 to be ablated while the medical imaging scan is performed. The navigational device 237 allows the physician to know whether or not the window portion 142 of the cannula 114 is located in the correct location for ablation. The navigational system can also provide information about whether the tissue 1003 to be ablated is close to a blood vessel, internal organ, or other anatomical feature.

As an alternative example, a navigational device such as a navigational marker or navigational sensor can be provided on the stylet 124. The navigational device in or on the stylet 124, such as at the tip of the stylet, is used to determine the location of the stylet 124. In some examples, the stylet 124 and cannula 114 can be locked together such that the stylet 124 and cannula 114 do not move with respect to one another during the process of positioning the introducer set 102 within the tissue. Thus, based on the determined location of the stylet 124, the location of the non-metal window portion 142 of the cannula 114 can be computed.

If the navigational device is present in the cannula 114, as in the example of FIG. 7, the navigational device 745 can be employed before or after the stylet 124 is removed from the cannula 114.

In some examples, before or after the stylet 124 is removed from the cannula 114, a fixation mechanism is deployed to fix the location of the cannula 114 in relation to the patient tissue 1001 and the tissue 1003 to be ablated.

After the introducer set 102 is inserted into the patient tissue and directed to the location of tissue to be ablated, the stylet 124 is removed from the cannula lumen 215. FIG. 11 is a cross-sectional view of the cannula 114 of FIG. 1 where the stylet 124 is no longer present in the lumen 215 of the cannula 114.

Figure 12:
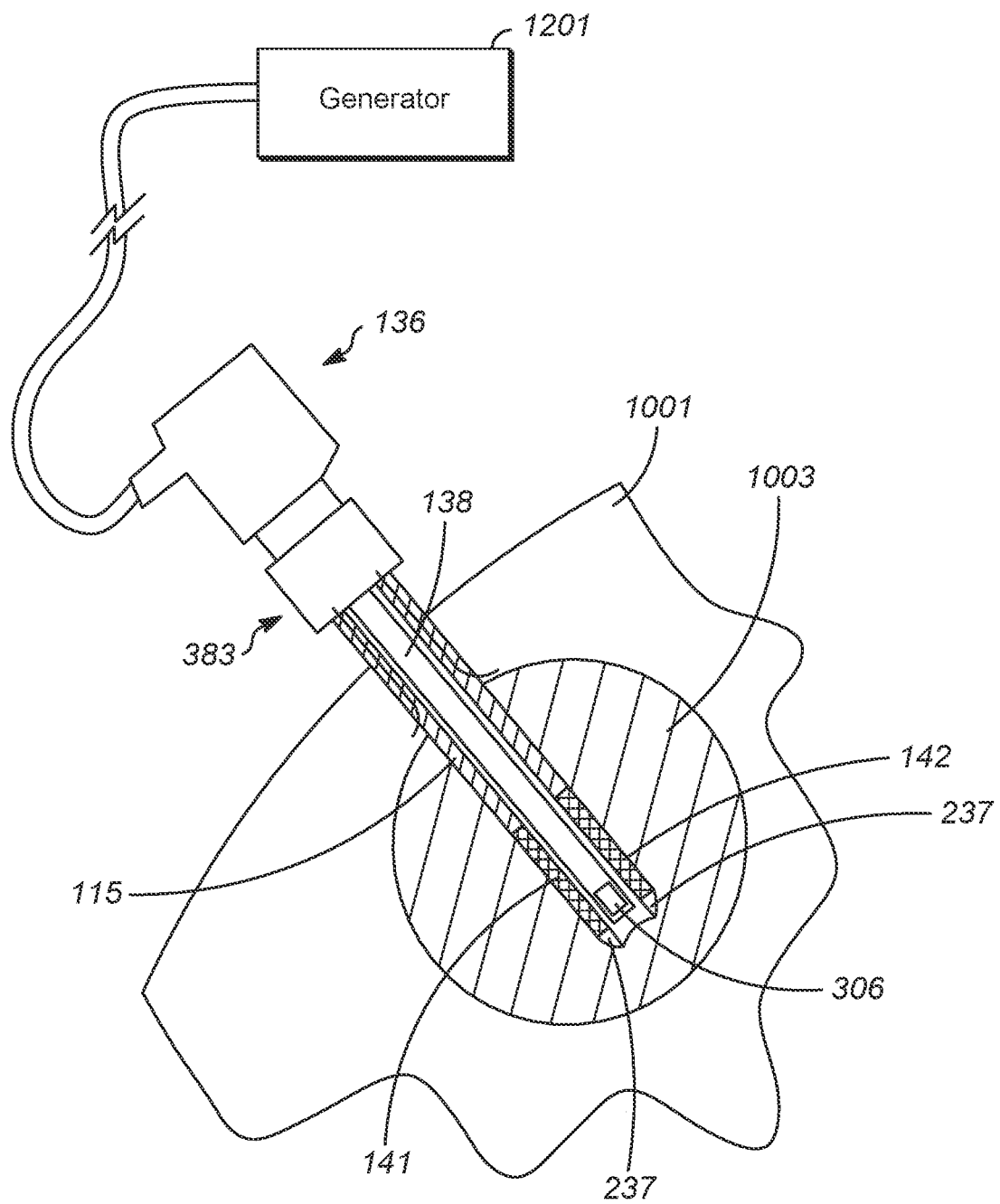
FIG. 12 is a cross-sectional view of the microwave ablation probe of FIG. 1 inserted into the cannula.

After the stylet 124 is removed from the cannula 114, the probe body 138 of a microwave ablation probe 136 is inserted into the lumen 215 of the cannula 114. FIG. 12 is a cross-sectional view of the microwave ablation probe 136 inserted into the cannula 114. In some examples, the microwave ablation probe 136 is inserted into the lumen 215 while the cannula 114 is fixed at a location in the tissue using a fixation mechanism. The probe body 138 is inserted into the lumen 215 and travels through the lumen 215 of the cannula body 115.

The radiating portion 306 of the microwave ablation probe 136 is aligned with a window portion 142 of the cannula 114 that is at least partially transparent to microwave energy. In some examples, the window portion 142 of the cannula is at least partially made of a non-metal material 141. In some examples, the radiating portion 306 of the microwave ablation probe 136 is moved into the lumen 215 of the cannula 114 such that the radiating portion 306 is near the distal end 218 of the cannula 114.

In some examples, a cannula-ablation probe connector 383 is employed to lock the cannula 114 and the microwave ablation probe 136 together. The cannula-ablation probe connector 383 can include a cannula connector 185 and a probe connector 189. In this case, the location of the cannula body 115 is fixed in relation to the probe body 138. In the examples in which a navigational system has been used to determine a location of the cannula 114 in patient tissue, the location of the window portion 142 of the cannula 114 in relation to the tissue 1003 to be ablated is known. The location of the radiating portion 306 of the microwave ablation probe 136 in relation to the window portion 142 of the cannula 114 is known. Therefore, the location of the radiating portion 306 with respect to the tissue 1003 to be ablated can be calculated.

In the example of FIG. 12, the microwave ablation probe 136 is operably connected to a power generator 1201. The power generator 1201 provides power to the microwave ablation probe 136. When power is transferred to the radiating portion 306 of the microwave ablation probe 136, microwave energy in the form of microwave radiation is emitted from the radiating portion 306 inside of the lumen 215. The microwaves travel through the transparent window portion 142, then exit the cannula body 115 and enter the tissue 1003 to be ablated, causing the tissue 1003 to heat and coagulate, thus killing the ablated cells. In the example of FIG. 12, the non-metal portion 141 overlaps the radiating portion 306 of the microwave ablation probe 136 while the surrounding tissue 1003 is being ablated.

In the example of FIG. 12, the microwave ablation probe 136 and the cannula 114 are locked together by a cannula-ablation probe connector 383. After ablation has been performed on the tissue 1003 to be ablated, in some examples, the microwave ablation probe 136 and cannula 114 are withdrawn from the patient's tissue simultaneously in the locked configuration. In some examples, ablation can be performed during removal of the microwave ablation probe 136 and cannula 114. This can prevent needle track seeding, where malignant cells are dragged through the tract created by the cannula 114 as the cannula 114 is removed from the patient tissue.

In some examples, before ablation, after ablation, or both before and after ablation, a biopsy sample of the tissue to be ablated can be removed through the cannula lumen 215. In some examples, a drug delivery catheter can be inserted into the cannula before the ablation procedure, after the ablation procedure, or both to deliver drug therapy.

After ablating a first location, the microwave ablation probe can be repositioned to a second, different location to apply microwave ablation therapy during a procedure. This may be done by removing the probe from the cannula, reinserting the stylet into the cannula, and repositioning the introducer set to the second location. Then, the stylet can be removed and the microwave ablation probe can be reinserted and apply microwave ablation therapy to the second location. This sequence can be repeated for additional therapy locations.

Alternatively, multiple introducer sets and microwave ablation probes can be inserted into a patient's tissue to provide ablation from multiple sources during a procedure.

The use of navigational devices in the introducer set, the microwave ablation probe, or both, along with an external navigation system, can provide imaging assistance and calculation assistance to map the positions of the multiple ablation probes and calculate the appropriate power settings based on the tumor or other tissue to be ablated.

It should be noted that, as used in this specification and the appended claims, the singular forms include the plural unless the context clearly dictates otherwise. It should also be noted that the term "or" is generally employed in its sense including "and/or" unless the content clearly dictates otherwise.

All publications and patent applications referenced in this specification are herein incorporated by reference in their entirety.

The disclosed technology has been described with reference to various example sand techniques. However, it should be understood that many variations and modifications may be made while remaining within the spirit and scope of the disclosed technology.

What is claimed is:

1. An introducer set comprising:
    a microwave ablation probe having an elongated probe body and a radiating portion for emission of microwave energy at a distal portion of the probe body;
    a cannula comprising:
        a cannula body defining a lumen sized to receive the elongated probe body of the microwave ablation probe,
        wherein the cannula body comprises a non-metal portion constructed from a non-metallic material located along the cannula body such that the non-metal portion overlaps the radiating portion of the microwave ablation probe when the microwave ablation probe is inserted into the cannula;
        wherein the cannula body further comprises a metal portion constructed from a metallic material, the metal portion spanning a proximal portion along the cannula body from a proximal end to the non-metal portion, wherein the metal portion does not overlap with the non-metal portion; and
    a tissue-penetrating stylet sized to be received by the lumen of the cannula;
    wherein the microwave ablation probe is configured to be fully housed in the cannula and to radiate microwave energy through the non-metal portion of the cannula body.

2. The introducer set of claim 1, wherein the stylet or the cannula further comprises at least one of a navigational sensor and a navigational marker.

3. The introducer set of claim 1 wherein the stylet further comprises a trocar at a tip of the stylet, wherein the cannula is less rigid than the stylet, and wherein the cannula comprises a blunt tip.

4. The introducer set of claim 1, wherein the elongated probe body comprises a blunt tip.

5. The introducer set of claim 1 further comprising a fixation mechanism configured to fix a location of at least a part of the cannula within or to patient tissue, the fixation mechanism comprising
    a plurality of tines for anchoring the cannula to tissue.

6. A microwave ablation system comprising:
a microwave ablation probe having an elongated probe body and a radiating portion for emission of microwave energy at a distal portion of the probe body; and
a cannula having:
   a cannula body comprising a first material that is not transparent to microwave energy;
   a lumen, and
   a window portion at a distal portion of the cannula body, the window portion comprising a material that is at least partially transparent to microwave energy;
wherein the microwave ablation probe is configured to be fully housed in the cannula such that the window portion of the cannula body overlaps the radiating portion of the microwave ablation probe, and to radiate microwave energy through the window portion of the cannula body, wherein the window portion does not overlap with the first material.

7. The microwave ablation system of claim 6, further comprising an introducer set comprising the cannula and a tissue-penetrating stylet sized to be received in the lumen of the cannula.

8. The microwave ablation system of claim 6 further comprising a fixation mechanism for fixing a location of the cannula within patient tissue.

9. The microwave ablation system of claim 6 wherein the window portion of the cannula overlaps the radiating portion of the microwave ablation probe at the distal portion of the probe body.

10. The microwave ablation system of claim 6, further comprising a connector configured to fix a position of the microwave ablation probe in relation to the cannula when the microwave ablation probe is inserted in the lumen of the cannula.

11. The microwave ablation system of claim 10, wherein the connector fixes the radiating portion of the microwave ablation probe in a position adjacent to the window portion of the cannula.

12. The microwave ablation system of claim 6 wherein the window portion comprises a non-metallic material.

13. The microwave ablation system of claim 12 wherein the non-metallic material is a dielectric polymer.

14. A microwave ablation method comprising:
inserting a microwave ablation probe into a lumen of a cannula;
aligning a radiating portion of the microwave ablation probe with a window portion of the cannula constructed from a material that is at least partially transparent to microwave energy;
causing microwave energy to be emitted from the radiating portion of the microwave ablation probe through the window portion of the cannula with the microwave ablation probe fully housed in the cannula and the window portion of the cannula body overlapping the radiating portion of the microwave ablation probe; and
blocking microwave radiation from radiating through a portion of the cannula constructed from a second material that is not transparent to microwave energy, wherein the window portion does not overlap with the second material.

15. The microwave ablation method of claim 14 further comprising:
inserting a tissue-piercing stylet into the lumen of the cannula;
piercing a body of tissue with the stylet while the stylet is inserted in the cannula lumen;
fixing the cannula at a location in the body of tissue;
removing the stylet from the cannula lumen;
inserting the microwave ablation probe into the lumen of the cannula while the cannula is fixed at the location in the tissue;
ablating the tissue with microwave energy emitted from the radiating portion of the microwave ablation probe.

16. The microwave ablation method of claim 15 further comprising:
removing a biopsy sample of the tissue through the cannula lumen.

17. The microwave ablation method of claim 14 further comprising:
fixing the microwave ablation probe to the cannula using a connector.

18. The introducer set of claim 5, wherein the plurality of tines are configured to be deployed from a retracted state in the tissue.

* * * * *